(12) United States Patent
Pokkalla et al.

(10) Patent No.: US 11,915,823 B1
(45) Date of Patent: *Feb. 27, 2024

(54) SYSTEMS AND METHODS FOR FRAME-BASED VALIDATION

(71) Applicant: PathAI, Inc., Boston, MA (US)

(72) Inventors: Harsha Vardhan Pokkalla, Allston, MA (US); Hunter L. Elliott, Boston, MA (US); Dayong Wang, Wellesley, MA (US); Benjamin P. Glass, Boston, MA (US); Ilan N. Wapinski, Brookline, MA (US); Jennifer K. Kerner, Brookline, MA (US); Andrew H. Beck, Brookline, MA (US); Aditya Khosla, Lexington, MA (US); Sai Chowdary Gullapally, Boston, MA (US); Ramprakash Srinivasan, Brookline, MA (US)

(73) Assignee: PathAI, Inc., Boston, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 17/984,866

(22) Filed: Nov. 10, 2022

Related U.S. Application Data

(63) Continuation of application No. 17/019,142, filed on Sep. 11, 2020, now Pat. No. 11,527,319.
(Continued)

(51) Int. Cl.
*G06K 9/00* (2022.01)
*G16H 30/40* (2018.01)
(Continued)

(52) U.S. Cl.
CPC ............ *G16H 30/40* (2018.01); *G06F 18/23* (2023.01); *G06N 3/08* (2013.01); *G16H 30/20* (2018.01); *G16H 50/20* (2018.01)

(58) Field of Classification Search
CPC ........ G16H 30/40; G16H 30/20; G16H 50/20; G06K 9/6218; G06N 3/08
See application file for complete search history.

(56) References Cited

U.S. PATENT DOCUMENTS 11,527,319 B1    12/2022 Pokkalla et al.
2016/0292855 A1 * 10/2016 Metzger ............... G06T 7/0012
(Continued)

FOREIGN PATENT DOCUMENTS

CA    3078672 A1 *  4/2019 ............. A61B 10/02
CA    3078672 A1     4/2019
(Continued)

*Primary Examiner* — Xin Jia
(74) *Attorney, Agent, or Firm* — Wolf, Greenfield & Sacks, P.C.

(57) ABSTRACT

In some aspects, the described systems and methods provide for validating performance of a model trained on a plurality of annotated pathology images. A pathology image is accessed. Frames are generated using the pathology image. Each frame in the set includes a distinct portion of the pathology image. Reference annotations are received from one or more users. The reference annotations describe at least one of a plurality of tissue or cellular characteristic categories for one or more frames in the set. Each frame in the set is processed using the trained model to generate model predictions. The model predictions describe at least one of the tissue or cellular characteristic categories for the processed frame. Performance of the trained model is validated based on determining a degree of association between the reference annotations and the model predictions for each frame and/or across all frames in the set of frames.

20 Claims, 5 Drawing Sheets

Related U.S. Application Data

(60) Provisional application No. 62/900,387, filed on Sep. 13, 2019.

(51) Int. Cl.
*G16H 30/20* (2018.01)
*G06N 3/08* (2023.01)
*G16H 50/20* (2018.01)
*G06F 18/23* (2023.01)

(56) References Cited

U.S. PATENT DOCUMENTS

2019/0220978 A1* 7/2019 Moehrle ............... G06T 7/0014
2020/0054306 A1* 2/2020 Mehanian ............ A61B 8/5223

FOREIGN PATENT DOCUMENTS

WO     WO 2020/096098 A1    5/2020
WO     WO-2020096098 A1 *   5/2020 ........... G06F 40/169

\* cited by examiner

300

SYSTEMS AND METHODS FOR FRAME-BASED VALIDATION

CROSS REFERENCE TO RELATED APPLICATIONS

This Application is a Continuation of U.S. patent application Ser. No. 17/019142, entitled "SYSTEMS AND METHODS FOR FRAME-BASED VALIDATION" and filed on Sep. 11, 2020, which claims priority under 35 U.S.C. § 119(e) to U.S. Provisional Application Ser. No. 62/900,387, entitled "SYSTEMS AND METHODS FOR FRAME-BASED VALIDATION" and filed on Sep. 13, 2019, each of these applications is herein incorporated by reference in its entirety.

BACKGROUND

The interpretation of cellular, molecular, and architectural features in histology samples plays an important role in the evaluation of disease states, including prognosis and treatment selection. This can include the assessment of the expression and localization of specific molecules relevant for a particular cancer treatment. For example, the evaluation of PD-L1 immunohistochemistry (IHC) expression in advanced urothelial cancer plays an important role in informing whether patients are strong candidates for anti-PD1 checkpoint inhibitors. In another example, the assessment of cellular and morphological features on Hematoxylin and Eosin (H&E)-stained samples allows evaluation of nuclear grade in tumor grade in renal cell carcinoma which can be prognostic of patient survival. Prior studies have shown that pathologists' manual and categorical scoring of many of these types of histological features is highly variable, both between pathologists on the same sample and for the same pathologist evaluating the same sample after a washout period.

SUMMARY

Understanding the variability described above requires methods by which the variability can be accurately, efficiently, and quantitatively measured. These measurements are not only useful in determining the reliability of existing manual interpretations but also in guiding the development of, and in validating, algorithmic approaches to histological assessment, e.g. those using machine learning or artificial intelligence. Accordingly, the inventors have appreciated that there is a need for the development of new methods to enable quantitative, standardized, and reproducible estimates during the evaluation of cellular, molecular, and/or architectural features (e.g., PD-L1 IHC expression or another suitable feature) in histology samples. For example, it may be difficult to use pathologists' slide-level assessment of PD-L1 IHC expression as a ground truth for concordance studies of quantitative measures of PD-L1 expression. Accordingly, the inventors have developed a platform to collect ground truth reference annotations of different cell types from a crowd-sourced network of pathologists in order to measure pathologist performance/consistency on this task, to validate the performance of a model, e.g., a deep learning based predictor, for predicting these cell types, and to compare pathologist performance with that of the model. While the systems and methods herein are described with respect to exemplary PD-L1 expression on cancer cells and/or immune cells, the described systems and methods are not so limited and may be equally suitable for other histology or pathology applications.

In some aspects, the described systems and methods provide for a method, a system, and/or a non-transitory computer-readable storage medium for validating performance of a model trained on a plurality of annotated pathology images, each of which includes at least one annotation describing tissue or cellular characteristic categories for one or more portions of the image. The method includes accessing a pathology image and generating a set of frames using the pathology image. Each frame in the set includes a distinct portion of the pathology image. Reference annotations are received from one or more users. The reference annotations describe at least one of a plurality of tissue or cellular characteristic categories for one or more frames in the set. Each frame in the set may be processed using the trained model to generate model predictions. The model predictions describe at least one of the plurality of tissue or cellular characteristic categories for the processed frame. Performance of the trained model is validated based on determining a degree of association between the reference annotations and the model predictions for each frame and/or across all frames in the set of frames.

In some embodiments, validating the performance of the trained model based on determining the degree of association between the reference annotations and the model predictions for each frame and/or across all frames in the set of frames comprises: aggregating the reference annotations from the one or more users spatially into a set of consensus clusters for each frame and/or across all frames in the set of frames, wherein one or more consensus annotations for the set of consensus clusters for each frame identify one or more tissue or cellular characteristic categories for the set of consensus clusters in the frame; associating the model predictions with a consensus annotation for a corresponding consensus cluster in the set of consensus clusters based on a measure of spatial proximity; estimating a true positive rate based on a proportion of the model predictions that correctly identify with the corresponding consensus annotations for the set of consensus clusters; and using the true positive rate to measure a degree of spatial association between the reference annotations and the model predictions for each frame and/or across all frames in the set of frames.

In some embodiments, the degree of association includes true positive rate, precision, recall, sensitivity and/or specificity of the trained model for each frame, aggregate of precision, recall, sensitivity and/or specificity of the trained model across the set of frames, and/or mean Average Precision (mAP) and mean Average Recall (mAR) of the trained model across a hyperparameter sweep of the trained model.

In some embodiments, validating performance of the trained model comprises: determining a consensus score based on the reference annotations from the one or more users for each frame in the set; determining a model score based on the model predictions for each frame in the set; and determining the degree of association between the reference annotations and the model predictions based on the consensus score and the model score for each frame in the set.

In some embodiments, the consensus score includes a median or mean value of scores based on the reference annotations relating to each user of the one or more users.

In some embodiments, the degree of association includes a Pearson correlation coefficient, a nonlinear rank correlation coefficient, and/or an intraclass correlation coefficient (ICC).

In some embodiments, validating performance of the trained model comprises: determining a user score for a particular user of the one or more users based on the reference annotations from the particular user for each frame in the set; determining a model score based on the model predictions for each frame in the set; and determining a degree of association between the reference annotations from the particular user and the model predictions based on the user score and the model score for each frame in the set.

In some embodiments, pathologist inter- and intra-observer variability may be evaluated by determining a degree of association between a plurality of pathologists and a consensus score determined by one or more distinct pathologists having evaluated the same frame or frames.

In some embodiments, generating the set of frames using the pathology image comprises: estimating a feature value for each frame in an initial set of randomly generated frames; and determining a distribution of feature values within the initial set of frames.

In some embodiments, the distribution of feature values is used to select a subset of the initial set of frames suitable for efficiently validating specific aspects of the model's or pathologist's performance.

In some embodiments, the selected frames are analyzed for inadequate quality, tissue staining, and/or presence of artifacts and one or more frames are excluded from the selected frames based on the analysis.

In some embodiments, receiving reference annotations for each frame in the set comprises: presenting, via a user interface, a frame from the set of frames to a user of the one or more users; receiving, via the user interface, at least one indication describing at least one of the plurality of tissue or cellular characteristic categories for the presented frame; and storing at least one reference annotation for the presented frame based on the indication.

In some embodiments, the frame is presented within a portion of the pathology image from which it was derived, wherein the portion of the pathology image is larger than the frame and includes the frame, and wherein the at least one indication is received within the presented frame.

In some embodiments, receiving reference annotations for each frame in the set comprises receiving exhaustive annotations for each frame from each of a plurality of pathologists.

In some embodiments, the reference annotations received from the one or more users for each frame in the set are used as ground truth data relating to the pathology image.

In some embodiments, processing, using the trained model, each frame in the set to generate model predictions, describing at least one of the plurality of tissue or cellular characteristic categories, for the processed frame comprises: processing, using the trained model, each frame in the set to generate model predictions, describing each of the plurality of tissue or cellular characteristic categories, for the processed frame.

In some embodiments, the accessed pathology image and/or the reference annotations are distinct from the plurality of annotated pathology images and/or respective annotations used to train the model.

In some embodiments, the accessed pathology image includes on the order of 10,000 to 1,000,000 cells. In some embodiments, small samples (e.g., biopsies) may have fewer than 10,000 cells. In some embodiments, large resections may have more than 1,000,000 cells.

In some embodiments, the plurality of tissue or cellular characteristic categories includes one or more categories selected from a group consisting of cancer epithelium, cancer stroma, normal tissue, necrosis, lymphoid, macrophage, lymphocyte, fibroblast, plasma cell, pulmonary macrophage, melanoma, pigmented macrophage, endothelial cell, mitotic figure, nucleoli, nuclear pleomorphism, nerve, adipocyte, peri-neural invasion, epithelial and epithelial tubule formation.

In some embodiments, the trained model comprises a convolutional neural network including a plurality of layers.

Further aspects of the technology may be understood based on the non-limiting illustrative embodiments described herein. While some embodiments described herein are described with respect to exemplary PD-L1 expression on cancer cells and/or immune cells, these embodiments may be equally suitable for other histology or pathology applications.

Still other aspects, embodiments, and advantages of these exemplary aspects and embodiments, are discussed in detail below. Any embodiment disclosed herein may be combined with any other embodiment in any manner consistent with at least one of the objects, aims, and needs disclosed herein, and references to "an embodiment," "some embodiments," "an alternate embodiment," "various embodiments," "one embodiment" or the like are not necessarily mutually exclusive and are intended to indicate that a particular feature, structure, or characteristic described in connection with the embodiment may be included in at least one embodiment. The appearances of such terms herein are not necessarily all referring to the same embodiment. The accompanying drawings are included to provide illustration and a further understanding of the various aspects and embodiments, and are incorporated in and constitute a part of this specification. The drawings, together with the remainder of the specification, serve to explain principles and operations of the described and claimed aspects and embodiments.

BRIEF DESCRIPTION OF THE DRAWINGS

Various aspects of at least one embodiment are discussed below with reference to the accompanying figures, which are not intended to be drawn to scale. Where technical features in the figures, detailed description or any claim are followed by reference signs, the reference signs have been included for the sole purpose of increasing the intelligibility of the figures, detailed description, and claims. Accordingly, neither the reference signs nor their absence is intended to have any limiting effect on the scope of any claim elements. For purposes of clarity, not every component may be labeled in every figure. The figures are provided for the purposes of illustration and explanation and are not intended as a definition of the limits of the invention. In the figures:

DETAILED DESCRIPTION

The systems and methods developed by the inventors collect ground truth reference annotations of different cell types from a crowd-sourced network of pathologists in order to validate the performance of a model, e.g., a deep learning based predictor, for predicting these cell types. The model may be trained on a plurality of annotated pathology images, each of which includes at least one annotation describing tissue or cellular characteristic categories for one or more portions of the image. The inventors have appreciated that a practical advantage of using a model, e.g., a deep learning based predictor, over manual pathology assessment, e.g., for quantitative analysis of PD-L1 expression, is that the model can be quantitative and/or highly scalable and can be applied to quantify, e.g., proportion of PD-L1 positivity, across hundreds-of-thousands of cells from sets of whole slide images across large patient cohorts.

Accordingly, some embodiments provide for a frame-based validation technique that involves: (1) accessing a pathology image; (2) generating a set of frames using the pathology image, wherein each frame in the set includes a distinct portion of the pathology image; (3) receiving, from one or more users, reference annotations, describing at least one of a plurality of tissue or cellular characteristic categories, for one or more frames in the set; (4) processing, using the trained model, each frame in the set to generate model predictions, describing at least one of the plurality of tissue or cellular characteristic categories, for the processed frame; and (5) validating performance of the trained model based on determining a degree of association between the reference annotations and the model predictions for each frame and/or across all frames in the set of frames.

The inventors have appreciated that, in cases where some or all of the frames are not distinct, e.g., the frames are overlapping and/or comprise the same region of the pathology image, the model is repeatedly evaluated on the same region of the pathology image instead of a diverse set of regions. Because this may lead to poor indication of model performance, care is taken to ensure that the frames are distinct, i.e., no two frames overlap with one another.

Throughout this disclosure, a convolutional neural network is used as an example of a model that may be used in accordance with some embodiments. However, it should be appreciated that other types of statistical models may alternatively be used, and embodiments are not limited in this respect. Other types of statistical models that may be used include a support vector machine, a neural network, a regression model, a random forest, a clustering model, a Bayesian network, reinforcement learning, metric learning, a genetic algorithm, or another suitable statistical model. More details for training the convolutional neural network are provided with respect to FIG. 3.

Figure 1:
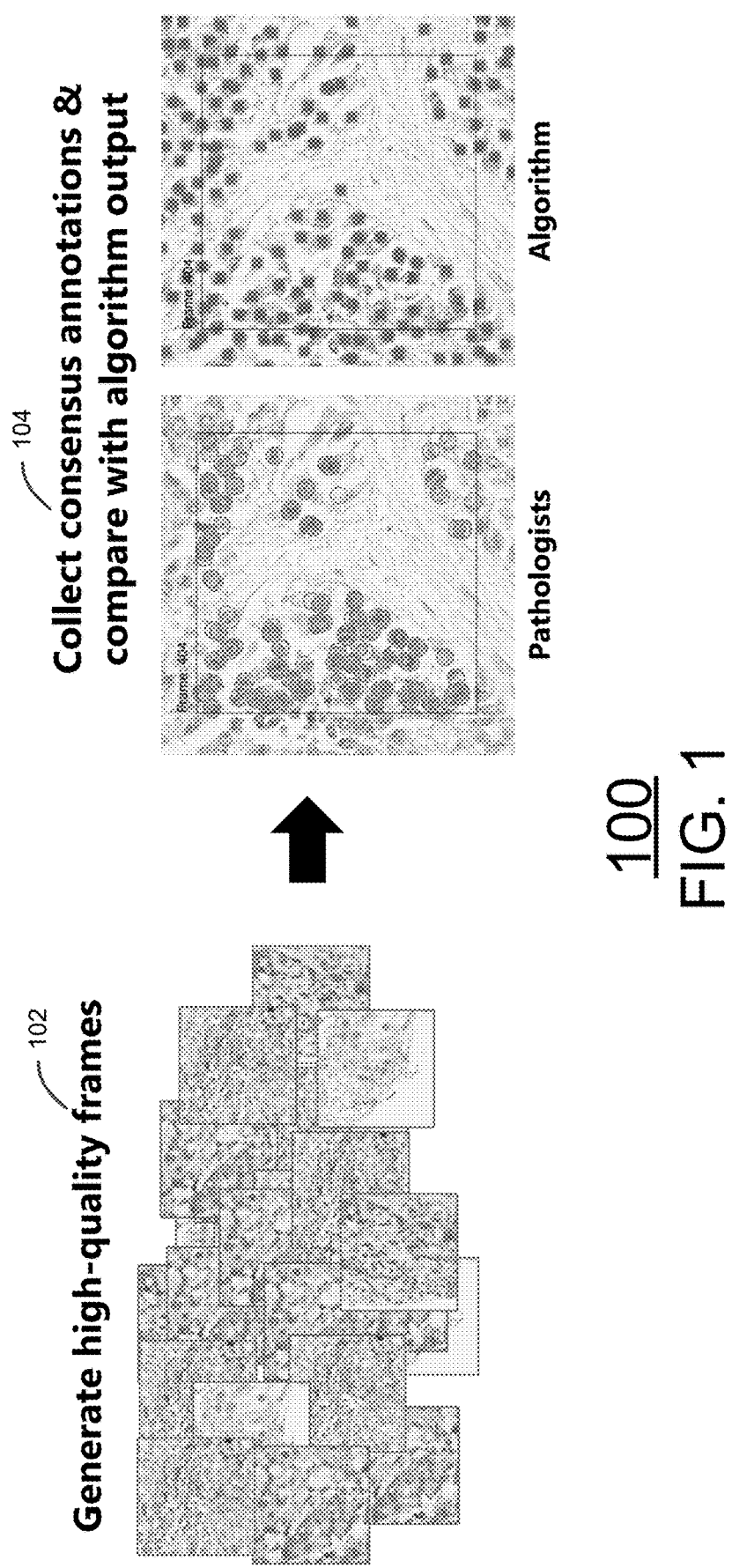
FIG. 1 shows a high-level diagram of a frame-based validation technique in accordance with some embodiments of the technology described herein.

FIG. 1 shows a high-level diagram 100 of a frame-based validation technique in accordance with some embodiments of the technology described herein. As discussed above, conventional approaches for generating ground truth data on whole slide images are limited, particularly for whole slide images that can contain ~10,000 to 1,000,000 individual cells, or another suitable number of cells. While computational systems are able to score essentially all cells in an image, pathologists are unable to exhaustively score all cells. Moreover, pathologists show significant inter- and intra-observer variability for whole slide estimates of quantitative scores (e.g., tumor grading, scoring IHC positivity, etc.). Thus, conventional pathologist estimates of whole slide image scores is a sub-optimal approach to obtain ground truth data for the evaluation of the performance of models, including image analysis algorithms. The inventors have appreciated that the herein described frames-based validation technique generates high-quality ground truth data from pathologists to use for assessing model performance and/or measuring pathologist variability. For example, at 102, high-quality frames can be generated by providing a small region of a slide where pathologists are able to provide high quality reference annotations on every individual cell. At 104, consensus annotations can be collected across a set of pathologists to ensure a high quality ground truth data set for comparing with model output and assessing model performance.

In one example, the described systems and methods may be used for quantitative assessment of PD-L1 expression in tumor cells and immune cells in advanced urothelial cancer (UC). In this example, a training set was provided with 309 cases of advanced UC for which a total of 105,514 reference annotations from 43 distinct pathologists were obtained. To generate a ground truth data set, exhaustive cellular reference annotations were obtained from a panel of five pathologists on a set of 80 sub-images (or frames) sampled uniformly across 10 bins of different cell densities within a validation data set of UC whole slide images. These were used to collect exhaustive reference annotations to produce quantitative pathologists' estimates of the proportion of PD-L1 positive tumor and immune cells on each frame. Altogether, 66,049 reference annotations for these consensus estimates were collected. These pathologists' estimates were used to compute pathologist consensus scores for each frame, and these consensus scores were correlated with each individual pathologist (i.e., inter-reader agreement) and with the prediction-based model scores (i.e., manual vs. predicted agreement). In the end, the prediction-based model scores showed significantly stronger correlation with the ground truth consensus scores than individual pathologists for quantifying the PD-L1 positivity proportion of lymphocytes (r2 0.744 vs. 0.598) and macrophages (r2 0.68 vs. 0.287). There was no statistically significant difference in correlation with consensus between prediction-based and individual pathologists for the quantification of PD-L1 positivity of tumor cells (r2 0.837 vs. 0.857).

Accordingly, the frames-based validation technique described herein represents a powerful and novel framework for validating model-based approaches in pathology. For example, data derived using this technique can confirm the relatively poor inter-reader agreement for immune-cell scoring, compared to tumor cell scoring, even when exhaustive frame-based scoring is employed. Further, data derived using this technique can demonstrate strong validation performance for the automated assessment of PD-L1 protein expression on tumor cells, lymphocytes, and macrophages using a model-based approach and may suggest that these model-powered measurements represent a more reproducible approach to assay interpretation.

Figure 2:
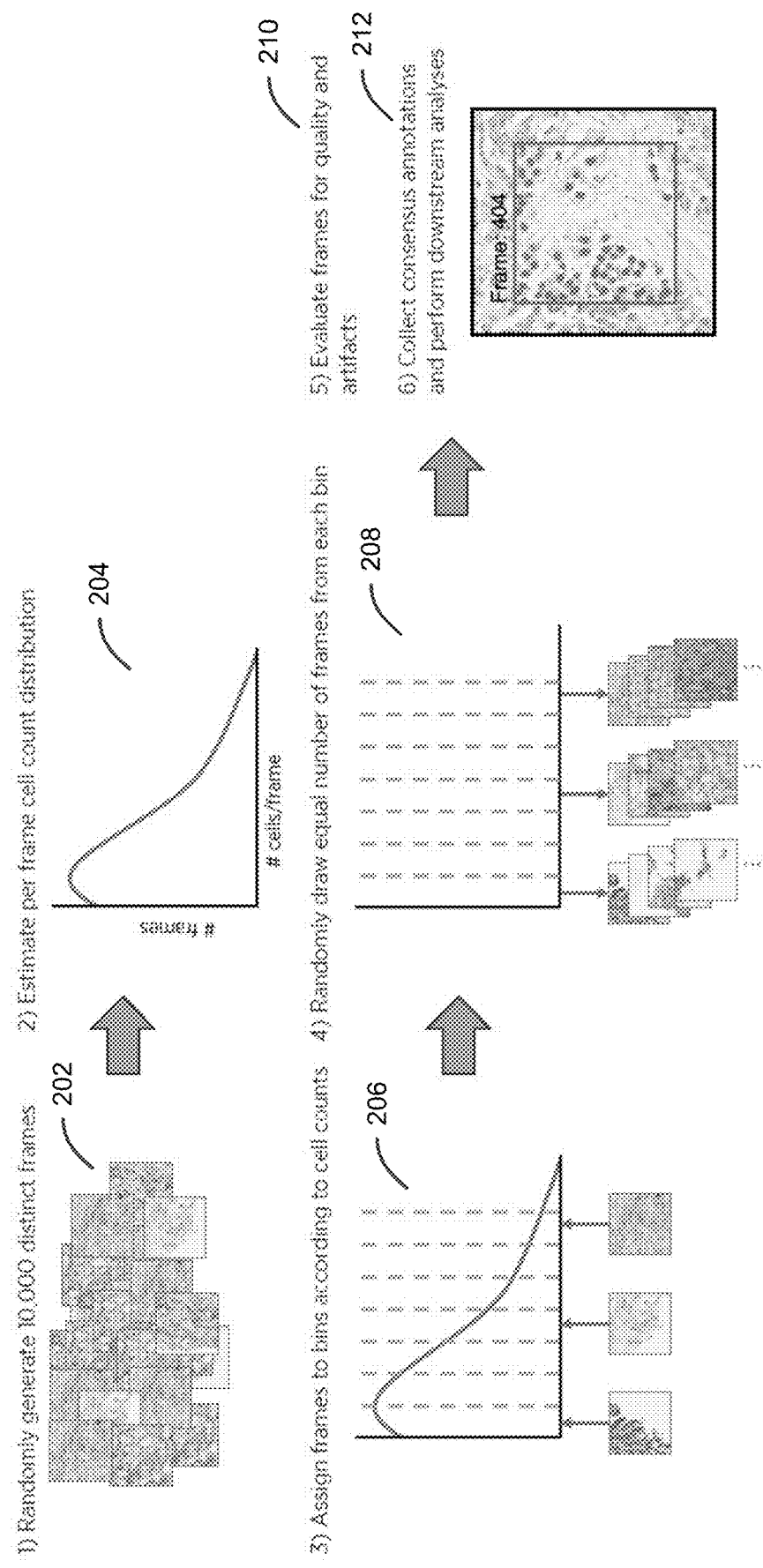
FIG. 2 shows a flow diagram of a frame selection procedure in accordance with some embodiments of the technology described herein.

FIG. 2 shows a flow diagram 200 of a frame selection procedure in accordance with some embodiments of the technology described herein. In order to generate a ground truth data set for concordance studies of quantitative measures of, e.g., PD-L1 expression, exhaustive cellular reference annotations may be obtained from a panel of pathologists on a set of sub-images (or frames) sampled from whole slide images from a validation data set (e.g., from a data set separated into a training set and a validation set). Frames may be sampled to optionally represent the full dynamic range of predicted cell counts per frame. The exhaustive reference annotations may be used to produce quantitative pathologists' estimates for each frame of, e.g., the proportion of PD-L1 positive cancer and immune cells. The pathologists' estimates may be used to compute pathologist consensus ground truth annotations and consensus scores for each frame. To evaluate model performance, these consensus scores may be correlated with the prediction-based model scores. Further, granular measures of spatial validity may be estimated by computing the true positive rate, precision, recall, sensitivity, and/or specificity of the model in recognizing the consensus ground truth annotations.

For the frame selection procedure, in order to obtain a concordance data set that represents a broad distribution of cell compositions across frames, frames may be selected using the following procedure. At 202, 10,000 distinct 300×300-pixel (or another suitable arrangement) frames are selected at random from regions of pathology images. At 204, cell count distributions are estimated for each of the selected frames. At 206, frames are separated into ten (or another suitable number) bins based on their predicted cellularity (ranging from low-cellularity to high-cellularity). At 208, 10 (or 12 or another suitable number) frames are randomly chosen from each bin pertaining to each trial to ensure a representative distribution of cellularity across the frames and trials. At 210, of the 100 (or 240 or another suitable number) resulting frames, frames that show inadequate quality, tissue staining, and/or presence of artifacts may be removed. At 212, of the remaining frames, 80 (or 100 or another suitable number) are randomly selected for analysis from each trial.

For pathologist data acquisition, each frame may be presented to a panel of pathologists using, e.g., a web-based platform. Pathologists may be given annotation instructions and tasked with identifying (and/or exhaustively marking) all cells of a given type within each frame. For example, data may be collected for cell types including, but not limited to, PD-L1 positive cancer cells, PD-L1 negative cancer cells, PD-L1 positive immune cells, and PD-L1 negative immune cells. In some embodiments, the results are shown to one or more pathologists via a user interface through which the pathologist can identify cells. The pathologist may provide reference annotations for regions (e.g., in the form of polygon annotations) or cells (e.g., in the form of point annotations) in a pathology image. The tissue or cellular characteristic category of the annotations may be specified to the pathologist, and input requested only for annotations of the specified tissue or cellular characteristic category, to ensure that the data is collected in a structured way instead of pathologists simply inputting text, e.g., tissue or cellular characteristic category, for each annotation they provide. For example, a user interface configured to display the pathology image may provide a drop down menu and/or a selection tool that enables the pathologist to select from among a fixed set of tissue or cellular characteristic categories.

In some embodiments, a consensus score is estimated based on the counts of cells. For example, for each frame, the consensus score may be computed for: number of PD-L1 positive immune cells, number of PD-L1 negative immune cells, proportion of PD-L1 positive immune cells (PD-L1 positive immune cells divided by the sum of PD-L1 positive and PD-L1 negative immune cells), number of PD-L1 positive cancer cells, number of PD-L1 negative cancer cells, and proportion of PD-L1 positive cancer cells (PD-L1 positive cancer cells divided by the sum of PD-L1 positive and PD-L1 negative cancer cells). Pearson correlation coefficient or another suitable metric (e.g., a nonlinear rank correlation coefficient, an intraclass correlation coefficient, etc.) may be computed between the prediction-based model scores and the pathologists' consensus scores for proportion of PD-L1 positive cancer cells and immune cells. To estimate the concordance of each pathologist with the pathologists' consensus, the consensus may be computed after removing that pathologist from the frame's cohort of annotations. To assess inter-pathologist agreement, the correlation of each pathologist's individual scores may be computed for proportion of PD-L1 positive cells with a consensus score generated from all the other pathologists. To assess agreement between model scores and the consensus score obtained from pathologist reference annotations, the Pearson correlation coefficient or another suitable metric may be computed between the model estimates of proportion of PD-L1 positive cells on each frame and the pathologists' consensus score on each frame.

In some embodiments, a robust consensus ground truth can be estimated by aggregating reference annotations of pathologists who have annotated that frame. This aggregation may be done on the basis of spatial proximity. For example, annotations may be aggregated from a plurality of pathologists into clusters based on a measure of spatial closeness, e.g., Euclidean distance or another suitable measure. Each cluster may be assigned a single indication based on the reference annotations that lie within this cluster. These cluster level indications may be treated as robust ground truth annotations. To estimate the concordance of the model with the pathologists' consensus, each model prediction may be assigned to a particular cluster based on the spatial closeness to the cluster, wherein the model's prediction and the cluster level indication may be compared for equality. Such comparisons may enable computation of metrics like true positive rate, precision, recall, sensitivity and/or specificity, at the level of individual frames, as well as aggregate precision and/or recall metrics over the entire set of frames. Further, measures such as mean Average Precision (mAP) and mean Average Recall (mAR), or another suitable measure, may be computed by varying hyperparameters of the model, e.g., hyperparameters of a CNN or another suitable statistical model. To estimate the concordance of each individual pathologist with the pathologists' consensus, the consensus reference annotations may be computed after removing that pathologist from the frame's cohort of annotations and subsequently redefining the clusters. Similar measures, such as precision and recall, may be computed to validate the performance of individual pathologists. It is appreciated that a variety of measures for comparing and evaluating model predictions to cluster level indications may be applied and the embodiments described herein are not limited in this respect.

Pathology images, histology images, or tissue images described herein may be microscopic images of tissue samples extracted from a patient. The images may be obtained by using an imaging instrument to create images of slides on which tissue slices are mounted. For example, the tissue slices mounted on the slides may have been taken from tissue samples, such as biopsy or autopsy specimens. The tissue samples may have been processed prior to capturing of images. For example, the tissue samples may have been fixed, stained, labeled, washed, or dehydrated. The samples may be taken from any tissue that indicates the presence or absence of a pathological condition. For example, the image may include a portion of a tumor. The image may be of a tissue that provides evidence of the presence or absence of a disease or condition, such as cancer, Alzheimer's disease, Parkinson's disease, diabetes, cystic fibrosis, sickle cell anemia, or an autoimmune disease. For example and without limitation, the tissue may be from a tumor or from the liver, lung, breast, ovary, uterus, cervix, vagina, testicle, spleen, lymph node, bladder, kidney, brain, esophagus, stomach, intestine, gall bladder, mouth, lip, nose, pancreas, prostate, colon, skin, or any other organ that may be suspected of having a tumor.

Tissue samples may include biopsied tissue obtained, for example, through core needle biopsy. The samples may be paraffin-embedded and may be sectioned into slices prior to staining. Tissue samples may be stained using any stain selected to highlight cellular structures or other features of interest useful in tissue analysis. The tissue samples may, for example, be prepared by hematoxylin and eosin stain (H&E stain). Examples of general staining methods include, but are not limited to, hematoxylin and eosin (H&E), trichrome, periodic acid Schiff (PAS), autoradiography, enzyme histochemistry, immuno-fluorescence, and immunohistochemistry (IHC). Specific stains include, but are not limited to, acid fuchsin, Aldehyde Fuchsin, Alician Blue, Alizarin Red S, Alkaline Phosphatase, aniline blue, Azan Stain, biebrich scarlet, Bielschowsky Stain, Cajal Stain, chromotrope 2R, Congo Red, Cresyl Violet, Eosin, fast green FCF, Fontana-Masson, Giemsa Stain, Golgi Stain, Gomori Trichrome, Heidenhain's AZAN trichrome stain, Hematoxylin, Iron Hematoxylin, light green SF yellowish, Luna Stain, Luxol Fast Blue, Mallory Trichrome, martius yellow, Masson Trichrome, Melanin Stains, methyl blue, milling yellow, Movat's Pentachrome, Mucicarmine, Mucin Stains, Myloperoxidase (MPO), Nissl Stains, Nuclear Fast Red, Oil Red 0, orange G, Orcien Stain, Osmium Tetroxide, Papanicolaou Stain, Perl's Iron Stain, phloxine, Phosphotungstic Acid-Hematoxylin (PTAH), picric acid, PicroSirius Red (polarized), ponceau 6R, Prussian Blue, Reticular Fiber Stain, Romanowsky Stains, Safranin 0, Schmorl's Stain, Silver Stains, Sudan Stains, Tartrazine, tartrazine, Toluidine Blue, Van Gieson, Verhoeff Stain, Von Kassa Stain, water blue, Weigert's Elastic Stain, Wright's Stain, and xylidine ponceau.

The tissue samples may be immune-stained with anti-cytokeratin antibody. The tissue samples may be prepared by yet other methods. For example, a tissue sample may be prepared by Papanicolaou stain (Pap stain). A sample could optionally be labeled by antibodies or probes, e.g., either of which could be fluorescently labeled or conjugated to elemental isotopes for mass spectrometry. Tissue staining may comprise IHC staining using, for example, labelled antibodies targeting proteins of interest or primary followed by secondary antibodies where the primary antibodies target proteins of interest and the secondary antibodies target the primary antibodies and carry, for example, a fluorescent or otherwise reporter detectable through known imaging techniques. Tissue staining such as immunohistochemistry may be performed on an automated platform such as those available from Ventana Medical Systems, Inc. (Tucson, Arizona). Tissue sample images may be captured using an imaging instrument such as a microscope and digital camera and corresponding software.

Any suitable imaging instrument may be used to obtain a pathology image, a histology image, or a tissue image, e.g., from a tissue sample on a slide. In some embodiments, a suitable imaging instrument includes an Olympus BX41 microscope in combination with a DP21 2 MP camera and CellSens software all available from Olympus Corporation (Center Valley, PA). Another suitable imaging instrument includes the Aperio ScanScope CS-0, Aperio AT2, and Aperio eSlide manager and web browser all available from Leica Biosystems, Inc. (Buffalo Grove, IL). Stained images may be acquired using, for example, a high resolution whole-slide scanner such as the Nanozoomer Whole Slide Scanner from Hamamatsu (Hamamatsu City, Shizuoka Pref., Japan). Once the images are acquired, either for training data or from a test sample, the image data may be provided to a system configured to process the image data using, for example, a statistical model.

In some embodiments, data sets for pathology images may be divided into training and validation sets. On the training data set, tissue region level reference annotations (e.g., melanoma tumor, stroma, necrosis, melanophage, background) and/or cellular reference annotations (e.g., PD-L1 positive immune cell, PD-L1 negative immune cell, PD-L1 positive cancer cell, PD-L1 negative cancer cell) may be obtained. These annotated image regions may be used to train a model, e.g., a tissue region classification model and/or a cell type and IHC positivity classification model. The model(s) may be applied to images from both the training and validation data sets to classify tissue regions and cell types, after which quantitative features may be extracted from each image (e.g., proportion of cancer cells that are PD-L1 positive, proportion of immune cells that are PD-L1 positive, and proportion of total cells (cancer cells and immune cells) that are PD-L1 positive).

Figure 3:
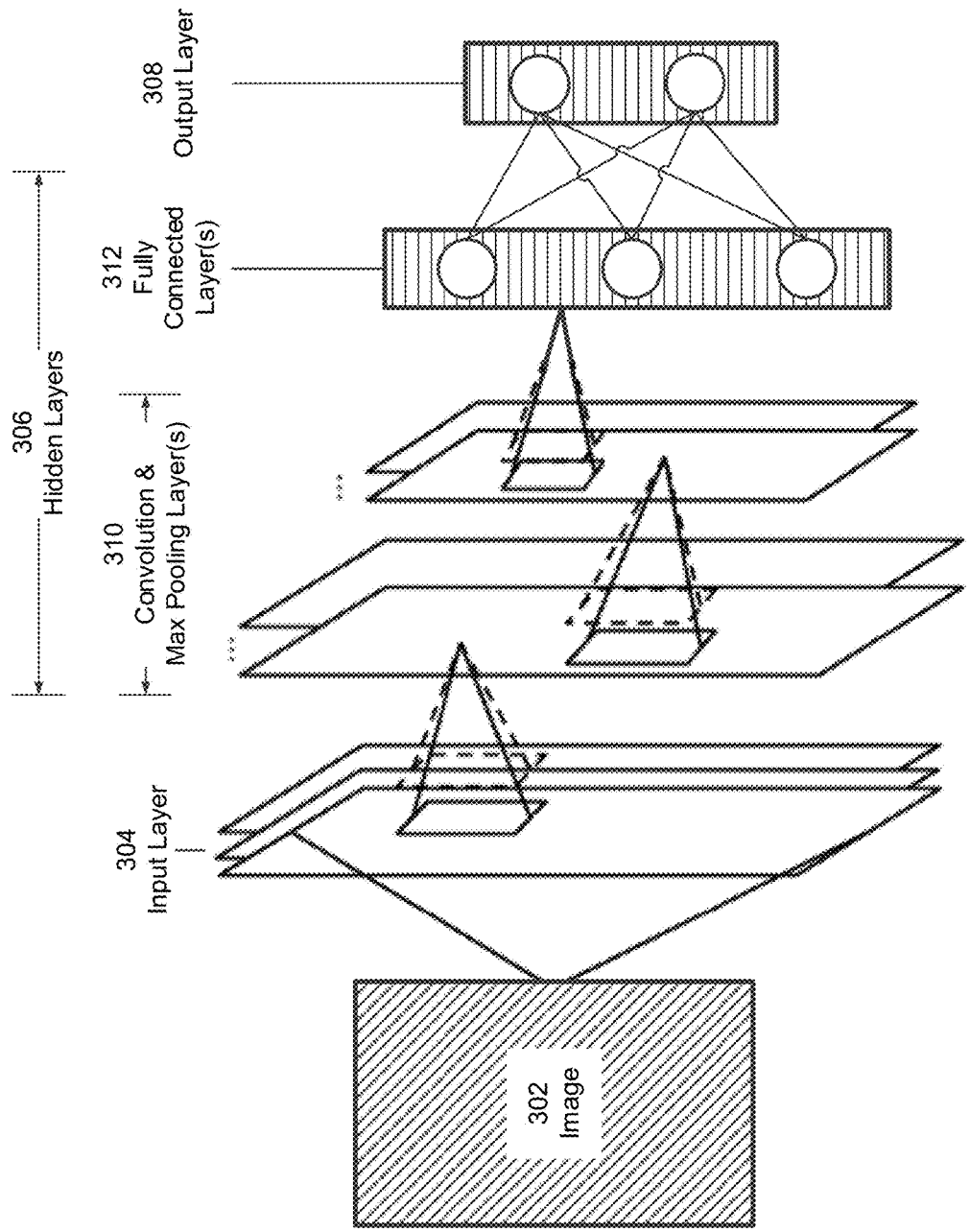
FIG. 3 schematically shows layers of a convolutional neural network in accordance with some embodiments of the technology described herein.

In some embodiments, the model may include a convolutional neural network. The convolutional neural network may be fully convolutional or may have one or more fully connected layers. In some embodiments, the model may be a different type of neural network model such as, for example, a recurrent neural network, a multi-layer perceptron, and/or a restricted Boltzmann machine. It should be appreciated that the model is not limited to being implemented as a neural network and, in some embodiments, may be a different type of model that may be used to predict annotations for one or more portions of a pathology image. For example, the model may be any suitable type of non-linear regression model such as a random forest regression model, a support vector regression model, or an adaptive basis function regression model. As another example, the model may be a Bayesian regression model or any other suitable Bayesian Hierarchical model. In some embodiments, a neural network includes an input layer, an output layer, and one or more hidden layers that define connections from the input layer to the output layer. Each layer may have one or more nodes. For example, the neural network may include at least 5 layers, at least 10 layers, at least 15 layers, at least 20 layers, at least 25 layers, at least 30 layers, at least 40 layers, at least 50 layers, or at least 100 layers. FIG. 3 provides details for training a convolutional neural network in accordance with some embodiments for model predictions of annotations for pathology images using the training data.

FIG. 3 shows a convolutional neural network 300 that may be used to predict annotations for a pathology image in accordance with some embodiments of the technology described herein. For example, convolutional neural network 300 may be used to predict annotations for a pathology image. The convolutional neural network may be used because such networks are suitable for analyzing visual images. The convolutional neural network may require no pre-processing of a visual image in order to analyze the visual image. As shown, the convolutional neural network comprises an input layer 304 configured to receive information about the image 302 (e.g., pixel values for all or one or more portions of a pathology image), an output layer 308 configured to provide the output (e.g., a classification), and a plurality of hidden layers 306 connected between the input layer 304 and the output layer 308. The plurality of hidden layers 306 include convolution and pooling layers 310 and fully connected layers 312.

The input layer 304 may be followed by one or more convolution and pooling layers 310. A convolutional layer may comprise a set of filters that are spatially smaller (e.g., have a smaller width and/or height) than the input to the convolutional layer (e.g., the image 302). Each of the filters may be convolved with the input to the convolutional layer to produce an activation map (e.g., a 2-dimensional activation map) indicative of the responses of that filter at every spatial position. The convolutional layer may be followed by a pooling layer that down-samples the output of a convolutional layer to reduce its dimensions. The pooling layer may use any of a variety of pooling techniques such as max pooling and/or global average pooling. In some embodiments, the down-sampling may be performed by the convolution layer itself (e.g., without a pooling layer) using striding.

The convolution and pooling layers 310 may be followed by fully connected layers 312. The fully connected layers 312 may comprise one or more layers each with one or more neurons that receives an input from a previous layer (e.g., a convolutional or pooling layer) and provides an output to a subsequent layer (e.g., the output layer 308). The fully connected layers 312 may be described as "dense" because each of the neurons in a given layer may receive an input from each neuron in a previous layer and provide an output to each neuron in a subsequent layer. The fully connected layers 312 may be followed by an output layer 308 that provides the output of the convolutional neural network. The output may be, for example, an indication of which class, from a set of classes, the image 302 (or any portion of the image 302) belongs to. The convolutional neural network may be trained using a stochastic gradient descent type algorithm or another suitable algorithm. The convolutional neural network may continue to be trained until the accuracy on a validation set (e.g., held out images from the training data) saturates or using any other suitable criterion or criteria.

It should be appreciated that the convolutional neural network shown in FIG. 3 is only one example implementation and that other implementations may be employed. For example, one or more layers may be added to or removed from the convolutional neural network shown in FIG. 3. Additional example layers that may be added to the convolutional neural network include: a pad layer, a concatenate layer, and an upscale layer. An upscale layer may be configured to upsample the input to the layer. An ReLU layer may be configured to apply a rectifier (sometimes referred to as a ramp function) as a transfer function to the input. A pad layer may be configured to change the size of the input to the layer by padding one or more dimensions of the input. A concatenate layer may be configured to combine multiple inputs (e.g., combine inputs from multiple layers) into a single output.

Convolutional neural networks may be employed to perform any of a variety of functions described herein. For example, a convolutional neural network may be employed to predict tissue or cellular characteristic categories for a pathology image. It should be appreciated that more than one convolutional neural network may be employed to make predictions in some embodiments. For example, a first convolutional neural network may be trained on a set of annotated pathology images and a second, different convolutional neural network may be trained on the same set of annotated pathology images, but magnified by a particular factor, such as 5×, 10×, 20×, or another suitable factor. The first and second neural networks may comprise a different arrangement of layers and/or be trained using different training data.

An example implementation of a convolutional neural network is illustrated below in Table 1. The convolutional neural network shown in Table 1 may be employed to classify an input image (e.g., a pathology image). For example, the convolutional network shown in Table 1 may be configured to receive an input pathology image of size 217 pixels by 217 pixels and provide an output that is indicative of one or more tissue or cellular characteristic categories or labels for the pathology image, e.g., four to eight tissue or cellular characteristic categories or labels. In Table 1, the sequence of the layers is denoted by the "Layer Number" column, the type of the layer is denoted by the "Layer Type" column, and the input to the layer is denoted by the "Input to Layer" column.

TABLE 1

Example Layer Configuration for Convolutional neural network

| Layer Number | Layer Type | # Filters/ Units | Filter Size | Stride | Activation Function | Dropout | Input to Layer |
|---|---|---|---|---|---|---|---|
| 1 | Input Layer | | | | | | Input Image |
| 2 | Convolution Layer | 96 | 7 | 3 | ReLU | | Output of Layer 1 |
| 3 | Pooling Layer | | 3 | 2 | | | Output of Layer 2 |
| 4 | Convolution Layer | 256 | 5 | 1 | ReLU | | Output of Layer 3 |
| 5 | Pooling Layer | | 3 | 2 | | | Output of Layer 4 |
| 6 | Convolution Layer | 384 | 3 | 1 | ReLU | | Output of Layer 5 |
| 7 | Convolution Layer | 384 | 3 | 1 | ReLU | | Output of Layer 6 |
| 8 | Convolution Layer | 256 | 3 | 1 | ReLU | | Output of Layer 7 |
| 9 | Pooling Layer | | 3 | 2 | ReLU | | Output of Layer 8 |
| 10 | Fully Connected Layer | 2048 | | | ReLU | dropout (0.5) | Output of Layer 9 |

TABLE 1-continued

Example Layer Configuration for Convolutional neural network

| Layer Number | Layer Type | # Filters/ Units | Filter Size | Stride | Activation Function | Dropout | Input to Layer |
|---|---|---|---|---|---|---|---|
| 11 | Fully Connected Layer | 2048 | | | ReLU | dropout (0.5) | Output of Layer 10 |
| 12 | Fully Connected Layer | # labels | | | softmax | | Output of Layer 11 |

Another example implementation of a convolutional neural network is illustrated below in Table 2. The convolutional neural network shown in Table 2 may be configured to receive an input pathology image of size 97 pixels by 97 pixels and provide an output that is indicative of one or more tissue or cellular characteristic categories or labels for the pathology image, e.g., four to eight tissue or cellular characteristic categories or labels. In Table 2, the sequence of the layers is denoted by the "Layer Number" column, the type of the layer is denoted by the "Layer Type" column, and the input to the layer is denoted by the "Input to Layer" column.

TABLE 2

Example Layer Configuration for Convolutional neural network

| Layer Number | Layer Type | # Filters/ Units | Filter Size | Stride | Activation Function | Dropout | Input to Layer |
|---|---|---|---|---|---|---|---|
| 1 | Input Layer | | | | | | Input Image |
| 2 | Convolution Layer | 96 | 7 | 3 | ReLU | | Output of Layer 1 |
| 3 | Pooling Layer | | 3 | 2 | | | Output of Layer 2 |
| 4 | Convolution Layer | 256 | 5 | 1 | ReLU | | Output of Layer 3 |
| 5 | Pooling Layer | | 3 | 1 | | | Output of Layer 4 |
| 6 | Convolution Layer | 256 | 3 | 1 | ReLU | | Output of Layer 5 |
| 7 | Convolution Layer | 256 | 3 | 1 | ReLU | | Output of Layer 6 |
| 8 | Convolution Layer | 256 | 3 | 1 | ReLU | | Output of Layer 7 |
| 9 | Pooling Layer | | 3 | 2 | | | Output of Layer 8 |
| 10 | Fully Connected Layer | 1024 | | | ReLU | dropout (0.5) | Output of Layer 9 |
| 11 | Fully Connected Layer | 1024 | | | ReLU | dropout (0.5) | Output of Layer 10 |
| 12 | Fully Connected Layer | # labels | | | softmax | | Output of Layer 11 |

In some embodiments, the convolutional neural network does not include padding between layers. The layers may be designed such that there is no overflow as pooling or convolution operations are performed. Moreover, layers may be designed to be aligned. For example, if a layer has an input of size N*N, and has a convolution filter of size K, with stride S, then (N−K)/S must be an integer in order to have perfect alignment.

Figure 4:
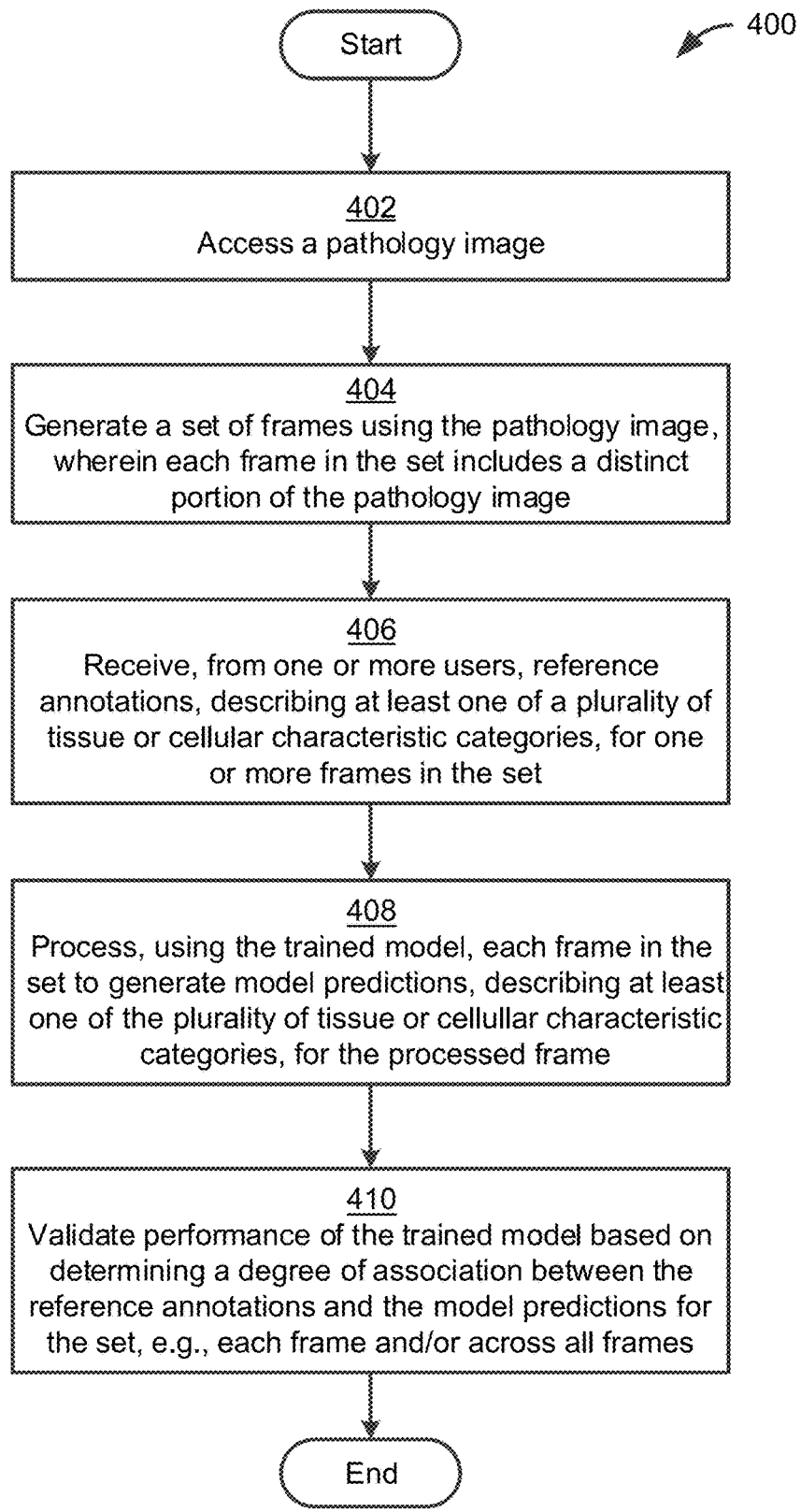
FIG. 4 shows a flowchart of an illustrative process for validating performance of a model trained on a plurality of annotated pathology images in accordance with some embodiments of the technology described herein.

FIG. 4 shows a flowchart 400 of an illustrative process for validating performance of a model trained on a plurality of annotated pathology images in accordance with some embodiments of the technology described herein. The model may be trained, for example, on annotated pathology images, each of which includes at least one annotation describing tissue or cellular characteristic categories for one or more portions of the image. The process for validating performance of the model may be implemented on system 500 of FIG. 5 or another suitable system or device.

At 402, a pathology image is accessed. In some embodiments, the accessed pathology image and/or the reference annotations are distinct from the plurality of annotated pathology images and/or respective annotations used to train the model. In some embodiments, the accessed pathology image includes on the order of 10,000 to 1,000,000 cells.

At 404, a set of frames is generated using the pathology image. Each frame in the set may include a distinct portion of the pathology image. For example, the set of frames may be generated as described with respect to FIG. 2. In some embodiments, generating the set of frames using the pathology image comprises: estimating a feature value for each frame in an initial set of randomly generated frames; and determining a distribution of feature values within the initial set of frames. In some embodiments, the distribution of feature values is used to select a subset of the initial set of frames suitable for efficiently validating specific aspects of the model's performance. In some embodiments, the selected frames are analyzed for inadequate quality, tissue staining, and/or presence of artifacts and one or more frames are excluded from the selected frames based on the analysis.

At 406, reference annotations are received from one or more users. The reference annotations may describe at least one of a plurality of tissue or cellular characteristic categories for one or more frames in the set. For example, the reference annotations may be received from one or more users as described with respect to FIG. 2. In some embodiments, receiving reference annotations for each frame in the set comprises receiving exhaustive annotations for each frame from each of a plurality of pathologists. In some embodiments, the reference annotations received from the one or more users for each frame in the set are used as ground truth data relating to the pathology image.

In some embodiments, receiving reference annotations for each frame in the set comprises: presenting, via a user interface, a frame from the set of frames to a user of the one or more users; receiving, via the user interface, at least one indication describing at least one of the plurality of tissue or cellular characteristic categories for the presented frame; and storing at least one reference annotation for the presented frame based on the indication. In some embodiments, the frame is presented within a portion of the pathology image from which it was derived, wherein the portion of the pathology image is larger than the frame and includes the frame, and wherein the at least one indication is received within the presented frame.

In some embodiments, the plurality of tissue or cellular characteristic categories includes one or more categories selected from a group consisting of cancer epithelium, cancer stroma, normal tissue, necrosis, lymphoid, macrophage, lymphocyte, fibroblast, plasma cell, pulmonary macrophage, melanoma, pigmented macrophage, endothelial cell, mitotic figure, nucleoli, nuclear pleomorphism, nerve, adipocyte, peri-neural invasion, epithelial and epithelial tubule formation.

At 408, each frame in the set is processed using the trained model to generate model predictions. The model predictions may describe at least one of the plurality of tissue or cellular characteristic categories for the processed frame. For example, the model predictions may be generated using a trained model as described with respect to FIG. 3. In some embodiments, the trained model comprises a convolutional neural network including a plurality of layers, or another suitable statistical model.

In some embodiments, processing, using the trained model, each frame in the set to generate model predictions, describing at least one of the plurality of tissue or cellular characteristic categories, for the processed frame comprises: processing, using the trained model, each frame in the set to generate model predictions, describing each of the plurality of tissue or cellular characteristic categories, for the processed frame.

At 410, performance of the trained model is validated based on determining a degree of association between the reference annotations and the model predictions for the set of frames, e.g., each frame in the set and/or across all frames. For example, the performance of the trained model may be validated based on consensus scores and prediction-based model scores, and by measuring a degree of spatial concordance between reference annotations and model predictions, as described with respect to FIG. 2.

In some embodiments, performance of the trained model is validated by aggregating the reference annotations from the one or more users spatially into a set of consensus clusters for each frame and/or across all frames in the set of frames. One or more consensus annotations for the set of consensus clusters for each frame may identify one or more tissue or cellular characteristic categories for the consensus clusters in the frame. The model predictions are associated with a consensus annotation for the corresponding consensus cluster in the set of consensus clusters based on a measure of spatial proximity. A true positive rate based on a proportion of the model predictions that correctly identify with the corresponding consensus annotations for the set of consensus clusters. Using the true positive rate, a degree of spatial association is measured between the reference annotations and the model predictions for each frame and/or across all frames in the set of frames. In a non-limiting example, for a model predicting a category of PD-L1 positive cancer cell, one way to obtain the true positive rate for the category of PD-L1 positive cancer cell is to determine a proportion of the model predictions that correctly identify with the consensus annotations for consensus clusters corresponding to the PD-L1 positive cancer cell category.

In some embodiments, the degree of association includes true positive rate, precision, recall, sensitivity and/or specificity of the trained model for each frame, aggregate of precision, recall, sensitivity and/or specificity of the trained model across the set of frames, and/or mean Average Precision (mAP) and mean Average Recall (mAR) of the trained model across a hyperparameter sweep of the trained model. The hyperparameter sweep may include varying the values of one or more hyperparameters of the model and retrieving model predictions for each variation of the model.

In some embodiments, performance of the trained model is validated by determining a consensus score based on the reference annotations from the one or more users for each frame in the set, determining a model score based on the model predictions for each frame in the set, and determining the degree of association between the reference annotations and the model predictions based on the consensus score and the model score for each frame in the set. In some embodiments, the consensus score includes a median or mean value of scores based on the reference annotations relating to each user of the one or more users. In some embodiments, the degree of association includes a Pearson correlation coefficient, a nonlinear rank correlation coefficient, and/or an intraclass correlation coefficient.

In some embodiments, performance of the trained model is validated by determining a user score for a particular user of the one or more users based on the reference annotations from the particular user for each frame in the set, determining a model score based on the model predictions for each frame in the set, and determining a degree of association between the reference annotations from the particular user and the model predictions based on the user score and the model score for each frame in the set.

Figure 5:
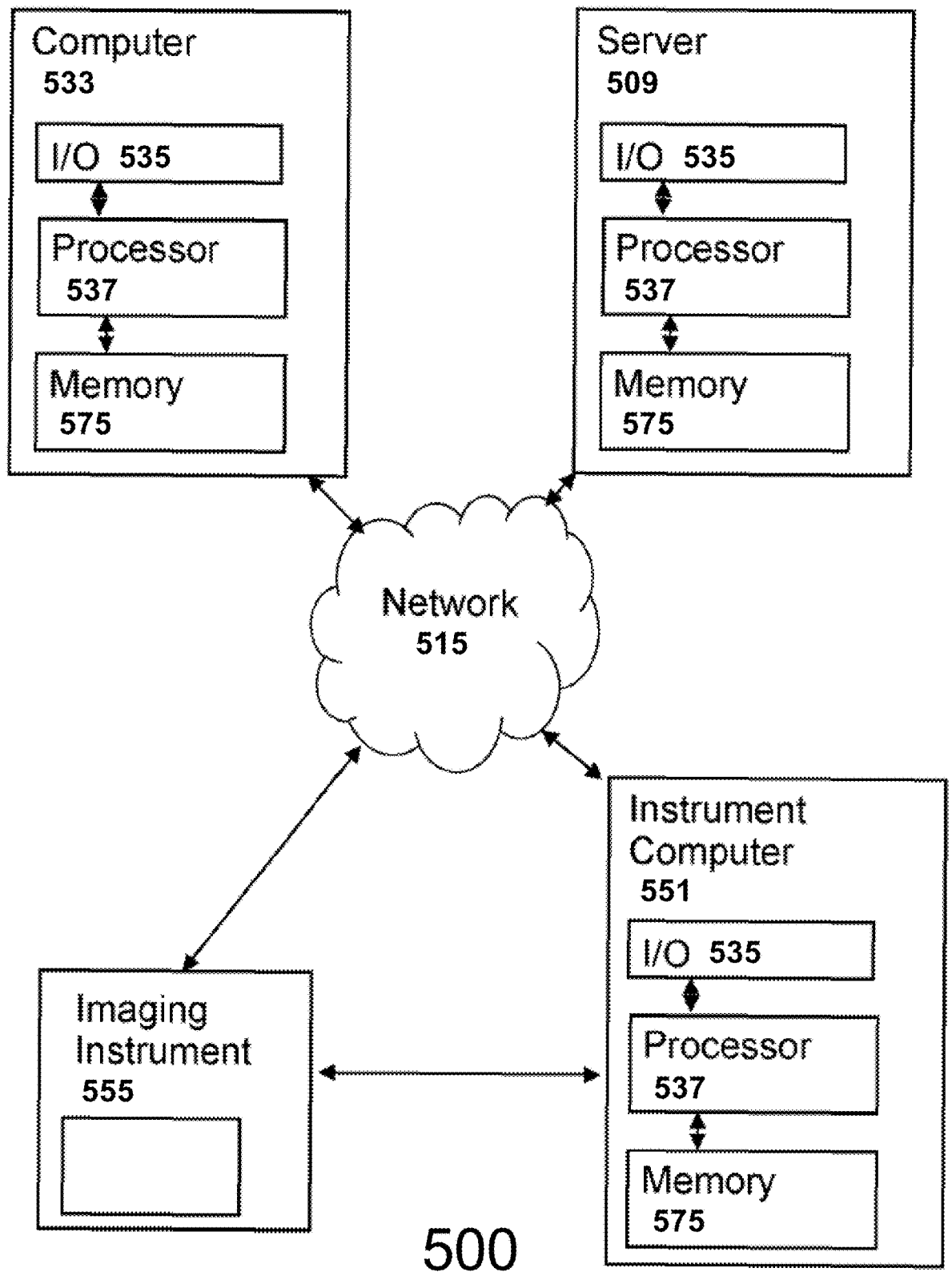
FIG. 5 shows a block diagram of a computer system on which various embodiments of the technology described herein may be practiced.

FIG. 5 shows a block diagram of a computer system on which various embodiments of the technology described herein may be practiced. The system 500 includes at least one computer 533. Optionally, the system 500 may further include one or more of a server computer 509 and an imaging instrument 555 (e.g., one of the instruments described above), which may be coupled to an instrument computer 551. Each computer in the system 500 includes a processor 537 coupled to a tangible, non-transitory memory device 575 and at least one input/output device 535. Thus the system 500 includes at least one processor 537 coupled to a memory subsystem 575 (e.g., a memory device or collection of memory devices). The components (e.g., computer, server, instrument computer, and imaging instrument) may be in communication over a network 515 that may be wired or wireless and wherein the components may be remotely located or located in close proximity to each other. Using those components, the system 500 is operable to receive or obtain image data such as pathology images, histology images, or tissue images and annotation and score data as well as test sample images generated by the imaging instrument or otherwise obtained. In certain embodiments, the system uses the memory to store the received data as well as the model data which may be trained and otherwise operated by the processor.

In some embodiments, some or all of system 500 is implemented in a cloud-based architecture. The cloud-based architecture may offer on-demand access to a shared pool of configurable computing resources (e.g. processors, graphics processors, memory, disk storage, network bandwidth, and other suitable resources). A processor in the cloud-based architecture may be operable to receive or obtain training data such as pathology images, histology images, or tissue images and annotation and score data as well as test sample images generated by the imaging instrument or otherwise obtained. A memory in the cloud-based architecture may store the received data as well as the model data which may be trained and otherwise operated by the processor. In some embodiments, the cloud-based architecture may provide a graphics processor for training the model in a faster and more efficient manner compared to a conventional processor.

Processor refers to any device or system of devices that performs processing operations. A processor will generally include a chip, such as a single core or multi-core chip (e.g., 12 cores), to provide a central processing unit (CPU). In certain embodiments, a processor may be a graphics processing unit (GPU) such as an NVidia Tesla K80 graphics card from NVIDIA Corporation (Santa Clara, CA). A processor may be provided by a chip from Intel or AMD. A processor may be any suitable processor such as the microprocessor sold under the trademark XEON E5-2620 v3 by Intel (Santa Clara, CA) or the microprocessor sold under the trademark OPTERON 6200 by AMD (Sunnyvale, CA). Computer systems may include multiple processors including CPUs and or GPUs that may perform different steps of the described methods. The memory subsystem 575 may contain one or any combination of memory devices. A memory device is a mechanical device that stores data or instructions in a machine-readable format. Memory may include one or more sets of instructions (e.g., software) which, when executed by one or more of the processors of the disclosed computers can accomplish some or all of the methods or functions described herein. Each computer may include a non-transitory memory device such as a solid state drive, flash drive, disk drive, hard drive, subscriber identity module (SIM) card, secure digital card (SD card), micro SD card, or solid state drive (SSD), optical and magnetic media, others, or a combination thereof. Using the described components, the system 500 is operable to produce a report and provide the report to a user via an input/output device. An input/output device is a mechanism or system for transferring data into or out of a computer. Exemplary input/output devices include a video display unit (e.g., a liquid crystal display (LCD) or a cathode ray tube (CRT)), a printer, an alphanumeric input device (e.g., a keyboard), a cursor control device (e.g., a mouse), a disk drive unit, a speaker, a touchscreen, an accelerometer, a microphone, a cellular radio frequency antenna, and a network interface device, which can be, for example, a network interface card (NIC), Wi-Fi card, or cellular modem.

It is to be appreciated that embodiments of the methods and apparatuses discussed herein are not limited in application to the details of construction and the arrangement of components set forth in the following description or illustrated in the accompanying drawings. The methods and apparatuses are capable of implementation in other embodiments and of being practiced or of being carried out in various ways. Examples of specific implementations are provided herein for illustrative purposes only and are not intended to be limiting. In particular, acts, elements and features discussed in connection with any one or more embodiments are not intended to be excluded from a similar role in any other embodiments.

Also, the phraseology and terminology used herein is for the purpose of description and should not be regarded as limiting. Any references to embodiments or elements or acts of the systems and methods herein referred to in the singular may also embrace embodiments including a plurality of these elements, and any references in plural to any embodiment or element or act herein may also embrace embodiments including only a single element. References in the singular or plural form are not intended to limit the presently disclosed systems or methods, their components, acts, or elements. The use herein of "including," "comprising," "having," "containing," "involving," and variations thereof is meant to encompass the items listed thereafter and equivalents thereof as well as additional items. References to "or" may be construed as inclusive so that any terms described using "or" may indicate any of a single, more than one, and all of the described terms. Any references to front and back, left and right, top and bottom, upper and lower, and vertical and horizontal are intended for convenience of description, not to limit the present systems and methods or their components to any one positional or spatial orientation.

Having thus described several aspects of at least one embodiment, it is to be appreciated that various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only.

References and citations to other documents, such as patents, patent applications, patent publications, journals, books, papers, web contents, have been made throughout this disclosure and in any patent applications incorporated by reference herein. All such documents are hereby incorporated herein by reference in their entirety for all purposes.

What is claimed is:

1. A method for validating performance of a trained model configured to predict at least one of a plurality of tissue and/or cellular characteristics categories from a pathology image, the method comprising, by at least a processor:

receiving, from a plurality of users, reference annotations each describing at least one of a plurality of tissue and/or cellular characteristic categories, for one or more frames in a set of frames for one or more pathology images, wherein each frame in the set of frames includes a portion of a pathology image of the one or more pathology images;

processing, using the trained model, the set of frames to generate model predictions of annotations each predicted annotation describing at least one of the plurality of tissue and/or cellular characteristic categories for a processed frame of the set of frames; and validating performance of the trained model based on determining a degree of association between the reference annotations and the model predicted annotations for the set of frames.

2. The method of claim 1, wherein:
determining the degree of association between the reference annotations and the model predicted annotations for the set of frames comprises:
for each of the plurality of users:
determining a respective concordance of the user with a respective user cluster comprising all other user(s) of the plurality of users by comparing the reference annotations of the user with the reference annotations of all other user(s) in the respective user cluster; and
determining a respective concordance of the model predictions with the respective user cluster by comparing the model predicted annotations with the reference annotations of all other user(s) in the respective user cluster; and
aggregating the concordances of the plurality of users and the concordances of the model predictions to determine the degree of association.

3. The method of claim 2, wherein comparing the reference annotations of the user with the reference annotations of all other user(s) in the respective user cluster comprises aggregating a plurality of pairwise comparisons each pairwise comparison comprising comparing a first reference annotation of the user and a second reference annotation of a user in the respective user cluster, wherein the first reference annotation and the second reference annotation are made for a same frame in the set of frames.

4. The method of claim 2, wherein:
determining the respective concordance of the user with the respective user cluster comprising all other user(s) of the plurality of users comprises using the reference annotations of all other user(s) in the respective user cluster as ground truth data against the reference annotations of the user; and
determining the respective concordance of the model predictions with the respective user cluster comprises using the reference annotations of all other user(s) in the respective user cluster as ground truth data against the model predicted annotations.

5. The method of claim 1, further comprising generating the set of frames using the one or more pathology images, by:
estimating a feature value for each frame in an initial set of randomly generated frames from the one or more pathology images; and
determining a distribution of feature values within the initial set of frames.

6. The method of claim 5, wherein the distribution of feature values is used to select a subset of the initial set of frames suitable for validating one or more aspects of the performance of the trained model.

7. The method of claim 6, wherein:
the feature value comprises a cell count; and
the subset of the initial set of frames are sampled uniformly across the distribution of feature values.

8. The method of claim 6, further comprising:
analyzing the selected frames for inadequate quality, tissue staining, and/or presence of artifacts; and
excluding one or more frames from the selected frames based on the analysis.

9. The method of claim 1, wherein the degree of association includes true positive rate, precision, recall, sensitivity and/or specificity of the trained model for each frame, aggregate of precision, recall, sensitivity and/or specificity of the trained model across the set of frames, and/or mean Average Precision (mAP) and mean Average Recall (mAR) of the trained model across a hyperparameter sweep of the trained model.

10. The method of claim 1, wherein receiving reference annotations for the one or more frames in the set of frames comprises:
presenting, via a user interface, an individual frame from the one or more frames in the set of frames to a user of the plurality of users;
receiving, via the user interface, at least one indication describing at least one of the plurality of tissue and/or cellular characteristic categories for the presented frame; and
storing at least one reference annotation for the presented frame based on the indication.

11. The method of claim 10, wherein the individual frame is presented within a portion of a pathology image of the one or more pathology images from which it was derived, wherein the portion of the pathology image is larger than the individual frame and includes the individual frame, and wherein the at least one indication is received within the presented frame.

12. The method of claim 1, wherein receiving reference annotations for the one or more frames in the set of frames comprises receiving exhaustive annotations for each of the one or more frames from a plurality of pathologists.

13. The method of claim 1, wherein the trained model is trained on a plurality of annotated pathology images, wherein each image of the plurality of annotated pathology images includes at least one annotation describing tissue and/or cellular characteristic categories for one or more portions of the image, and wherein the plurality of annotated pathology images are distinct from the one or more pathology images for validation, and wherein the at least one annotation of each image of the plurality of annotated images are distinct from the reference annotations for the one or more pathology images from the plurality of users.

14. The method of claim 1, wherein the one or more pathology images each include a number of cells on an order of 10,000 to 1,000,000 cells.

15. The method of claim 1, wherein the plurality of tissue and/or cellular characteristic categories include one or more categories of cancer epithelium, cancer stroma, normal tissue, necrosis, lymphoid, macrophage, lymphocyte, fibroblast, plasma cell, pulmonary macrophage, melanoma, pigmented macrophage, endothelial cell, mitotic figure, nucleoli, nuclear pleomorphism, nerve, adipocyte, peri-neural invasion, epithelial or epithelial tubule formation.

16. The method of claim 1, wherein the trained model comprises a convolutional neural network including a plurality of layers.

17. A system for validating performance of a trained model configured to predict at least one of a plurality of tissue and/or cellular characteristics categories from a pathology image, the system comprising:
at least one computer hardware processor; and
at least one non-transitory computer-readable storage medium storing processor-executable instructions that, when executed by the at least one computer hardware processor, cause the at least one computer hardware processor to perform:
receiving, from a plurality of users, reference annotations each describing at least one of a plurality of tissue and/or cellular characteristic categories, for one or more frames in a set of frames for one or more pathology images, wherein each frame in the set of frames includes a portion of a pathology image of the one or more pathology images;

processing, using the trained model, the set of frames to generate model predictions of annotations, each predicted annotations describing at least one of the plurality of tissue and/or cellular characteristic categories, for a processed frame of the set of frames; and validating performance of the trained model based on determining a degree of association between the reference annotations and the model predicted annotations for the set of frames.

18. The system of claim 17, wherein:

determining the degree of association between the reference annotations and the model predicted annotations for the set of frames comprises:

for each of the plurality of users:
- determining a respective concordance of the user with a respective user cluster comprising all other user(s) of the plurality of users by comparing the reference annotations of the user with the reference annotations of all other user(s) in the respective user cluster; and
- determining a respective concordance of the model predictions with the respective user cluster by comparing the model predicted annotations with the reference annotations of all other user(s) in the respective user cluster; and aggregating the concordances of the plurality of users and the concordances of the model predictions to determine the degree of association.

19. At least one non-transitory computer-readable storage medium storing processor-executable instructions that, when executed by at least one computer hardware processor, cause the at least one computer hardware processor to perform a method for validating performance of a trained model configured to predict at least one of a plurality of tissue and/or cellular characteristics categories from a pathology image, the method comprising:

receiving, from a plurality of users, reference annotations each describing at least one of a plurality of tissue and/or cellular characteristic categories, for one or more frames in a set of frames for one or more pathology images, wherein each frame in the set of frames includes a portion of a pathology image of the one or more pathology images;

processing, using the trained model, the set of frames to generate model predictions of annotations, each predicted annotation describing at least one of the plurality of tissue and/or cellular characteristic categories, for a processed frame of the set of frames; and validating performance of the trained model based on determining a degree of association between the reference annotations and the model predicted annotations for the set of frames.

20. The storage medium of claim 19, wherein:

determining the degree of association between the reference annotations and the model predicted annotations for the set of frames comprises:

for each of the plurality of users:
- determining a respective concordance of the user with a respective user cluster comprising all other user(s) of the plurality of users by comparing the reference annotations of the user with the reference annotations of all other user(s) in the respective user cluster; and
- determining a respective concordance of the model predictions with the respective user cluster by comparing the model predicted annotations with the reference annotations of all other user(s) in the respective user cluster; and aggregating the concordances of the plurality of users and the concordances of the model predictions to determine the degree of association.

\* \* \* \* \*